United States Patent
Koester

(10) Patent No.: US 9,289,616 B2
(45) Date of Patent: Mar. 22, 2016

(54) PARTICULATE TOUGHENED CERAMIC FEEDTHROUGH

(75) Inventor: Kurt J. Koester, Los Angeles, CA (US)

(73) Assignee: ADVANCED BIONICS AG, Staefa (CH)

( * ) Notice: Subject to any disclaimer, the term of this patent is extended or adjusted under 35 U.S.C. 154(b) by 109 days.

(21) Appl. No.: 13/993,162

(22) PCT Filed: Dec. 14, 2011

(86) PCT No.: PCT/US2011/064876
§ 371 (c)(1),
(2), (4) Date: Aug. 19, 2013

(87) PCT Pub. No.: WO2012/082878
PCT Pub. Date: Jun. 21, 2012

(65) Prior Publication Data
US 2013/0331923 A1    Dec. 12, 2013

Related U.S. Application Data

(60) Provisional application No. 61/423,355, filed on Dec. 15, 2010.

(51) Int. Cl.
*A61N 1/375* (2006.01)
*A61N 1/05* (2006.01)
*A61N 1/02* (2006.01)

(52) U.S. Cl.
CPC ........... *A61N 1/3754* (2013.01); *A61N 1/0541* (2013.01); *Y10T 29/49002* (2015.01)

(58) Field of Classification Search
CPC ....... A61N 1/025; A61N 1/05; A61N 1/0541; A61N 1/375; A61N 1/3752; A61N 1/3754

USPC ............ 607/2, 137; 174/50.53, 650; 29/592.1
See application file for complete search history.

(56) References Cited

U.S. PATENT DOCUMENTS

| | | | | |
|---|---|---|---|---|
| 3,743,569 A | * | 7/1973 | Wilkens | C04B 35/71 109/49.5 |
| 4,486,514 A | * | 12/1984 | Chaney, Jr. | 429/56 |
| 4,732,780 A | | 3/1988 | Mitoff et al. | |
| 4,816,621 A | * | 3/1989 | Huebner et al. | 174/152 GM |

(Continued)

FOREIGN PATENT DOCUMENTS

| EP | 0441528 | 10/1996 |
|---|---|---|
| EP | 0887838 | 12/1998 |

(Continued)

OTHER PUBLICATIONS

Becher, "Microstructural Design of Toughened Ceramics," J. Am. Ceram. Soc., 74[2] 255-69, Feb. 1991.

(Continued)

*Primary Examiner* — Christopher A Flory
(74) *Attorney, Agent, or Firm* — Fabian Vancott; Steven L. Nichols

(57) ABSTRACT

A feedthrough includes a ceramic body mechanically joined about a perimeter to a hermetic case. The ceramic body includes a ceramic matrix and a ductile phase distributed through at least a portion of the ceramic matrix. The ductile phase increases the resistance of the ceramic matrix to crack propagation. A plurality of electrical conductors passes through the ceramic body.

20 Claims, 6 Drawing Sheets

(56) References Cited

U.S. PATENT DOCUMENTS

| | | | |
|---|---|---|---|
| 4,837,230 | A | 6/1989 | Chen et al. |
| 4,841,098 | A * | 6/1989 | Dunton .................. 174/15.3 |
| 4,857,746 | A * | 8/1989 | Kuhlmann et al. ............ 438/24 |
| 5,045,402 | A | 9/1991 | Adams, Jr. et al. |
| 5,198,094 | A * | 3/1993 | Mettes .................. 204/430 |
| 5,272,283 | A * | 12/1993 | Kuzma .................. 174/262 |
| 5,304,517 | A | 4/1994 | Casey et al. |
| 5,406,444 | A * | 4/1995 | Selfried et al. ............ 361/302 |
| 5,591,287 | A | 1/1997 | Clegg et al. |
| 5,835,841 | A * | 11/1998 | Yamada ............ B22F 1/0096 419/10 |
| 5,978,204 | A * | 11/1999 | Stevenson ............ 361/303 |
| 6,020,685 | A * | 2/2000 | Wei et al. ............ 313/625 |
| 6,245,439 | B1 * | 6/2001 | Yamada ........... C04B 35/62695 264/109 |
| 6,414,835 | B1 | 7/2002 | Wolf et al. |
| 6,548,011 | B1 | 4/2003 | Rhee et al. |
| 7,564,674 | B2 | 7/2009 | Frysz et al. |
| 7,569,452 | B2 | 8/2009 | Fu et al. |
| 8,386,047 | B2 * | 2/2013 | Koester .................. 607/57 |
| 8,552,311 | B2 * | 10/2013 | Koester et al. ............ 174/262 |
| 2003/0007310 | A1 | 1/2003 | Trinh et al. |
| 2004/0256031 | A1 * | 12/2004 | Kim .................. C22C 45/001 148/403 |
| 2006/0023397 | A1 * | 2/2006 | Brendel .................. 361/302 |
| 2006/0071597 | A1 | 4/2006 | Gootzen et al. |
| 2006/0244165 | A1 * | 11/2006 | Huang ............... C04B 35/522 264/29.5 |
| 2006/0259093 | A1 * | 11/2006 | Stevenson et al. ............ 607/37 |
| 2007/0053137 | A1 | 3/2007 | Fu et al. |
| 2007/0123766 | A1 | 5/2007 | Whalen, III et al. |
| 2007/0183117 | A1 | 8/2007 | Fu et al. |
| 2007/0183118 | A1 | 8/2007 | Fu et al. |
| 2007/0207186 | A1 * | 9/2007 | Scanlon .................. A61F 2/07 424/424 |
| 2007/0217121 | A1 | 9/2007 | Fu et al. |
| 2007/0277374 | A1 * | 12/2007 | Suaning .................. 29/831 |
| 2009/0229648 | A1 * | 9/2009 | Makansi ............... B82Y 10/00 136/201 |
| 2009/0322221 | A1 * | 12/2009 | Makansi ............... F25B 21/00 313/523 |
| 2011/0048770 | A1 | 3/2011 | Reiterer et al. ...... 174/152 GM |
| 2012/0058882 | A1 | 3/2012 | Kaplan ............... C04B 35/117 501/88 |
| 2012/0127627 | A1 * | 5/2012 | Brendel et al. ............ 361/302 |
| 2013/0100595 | A1 * | 4/2013 | Koester et al. .......... 361/679.01 |
| 2013/0230424 | A1 * | 9/2013 | Reiterer et al. ................ 419/8 |
| 2014/0309510 | A1 * | 10/2014 | Lucisano et al. ............ 600/347 |

FOREIGN PATENT DOCUMENTS

| | | |
|---|---|---|
| EP | 1760735 | 3/2007 |
| EP | 1796115 A2 | 6/2007 |
| EP | 1820534 A2 | 8/2007 |
| EP | 1834666 A2 | 9/2007 |
| EP | 1796115 A3 | 3/2009 |
| EP | 2193823 | 9/2010 |
| JP | 10194856 | 7/1998 |
| JP | 2006222441 | 8/2006 |

OTHER PUBLICATIONS

Calvert et al., "Toughness in Synthetic and Biological Multilayered Systems,"; Department of Materials Science and Engineering, University of Arizona, Tucson AZ 85712; available at: http://tesumassd.org/faculty/calvert/papers/roysoc.pdf.; p. 1-19; Feb. 15, 2002.

Clegg et al., "Ductile Particle Toughening of Hydroxyapatite Ceramics Using Platinum Particles," SIF2004 Structural Integrity and Fracture International Conference; pp. 47-53; Sep. 26, 2004.

Evans, "Perspective on the Development of High-Toughness Ceramics," J. Am. Ceram. Soc., 73[2] 187-206, Feb. 1990.

Hussain et al., "Electrical conductivity of an insulator matrix (alumina) and conductor particle (molybdenum) composites,"; Trieste, Italy; English abstract only, Aug. 29, 2002.

Jiang et al., "Technology Advances and Challenges in Hermetic Packaging for Implantable Medical Devices," D.D. Zhou, E. Greenbaum (eds.), Implantable Neural Prostheses 2, 27, Biological and Medical Physics, Biomedical Engineering, DOI 10.1007/978-0-387-98120-8_2, C_Springer Science+Business Media, LLC 2010; pp. 27-61.

Kruzic, "Interfacial and near interfacial crack growth phenomena in metal bonded alumina,"; Lawrence Berkeley National Laboratory; http:escholarship.org/uc/item/5f44d047, Mar. 1, 2002; pp. 1-121.

Pastorino-Chassale et al., "Production, microstructural comparison and mechanical behavior of reinforced alumina composites containing zirconia, silicon carbide, nickel and titanium", Journal of Ceramic Processing Research. vol. 11, No. 3, pp. 372-376, Aug. 25, 2010.

Rao et al., "Laminar Ceramics That Exhibit a Threshold Strength," www.sciencemag.org, Science, vol. 286, Oct. 1, 1999.

Roether et al., "Dispersion-Reinforced Glass and Glass-Ceramic Matrix Composites," Handbook of Ceramic Composites, copyright 2005, p. 489.

Sun et al., "Ductile Phase Toughened Brittle Materials," J. Mater. Sci. Technol., vol. 12, Feb. 1996.

* cited by examiner

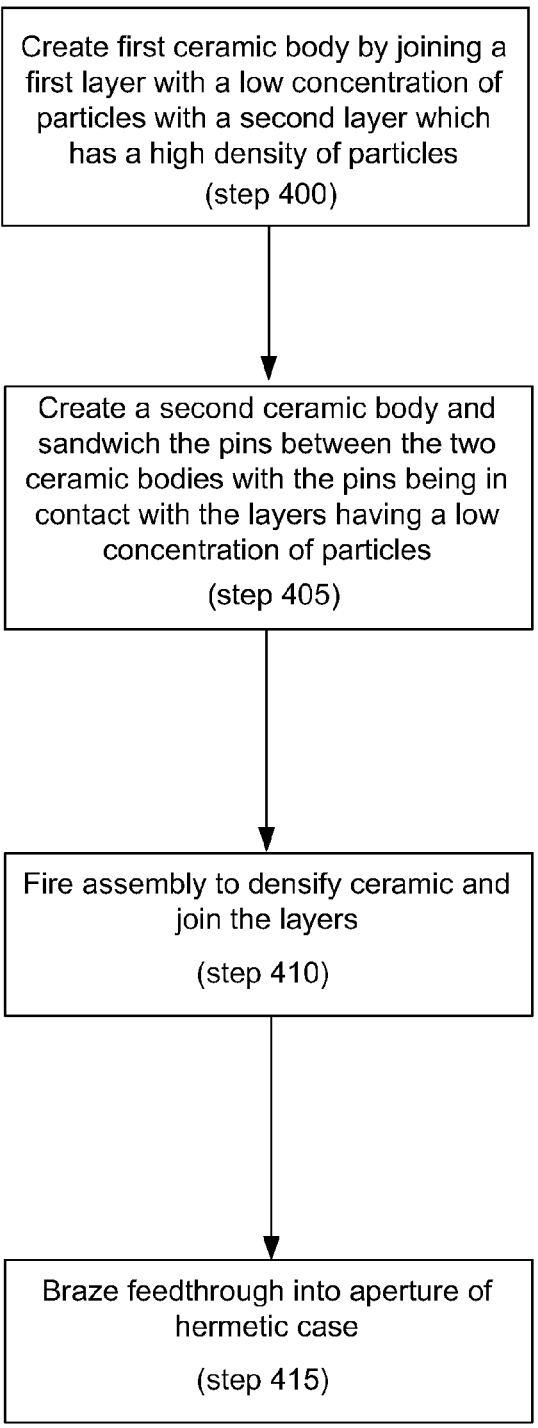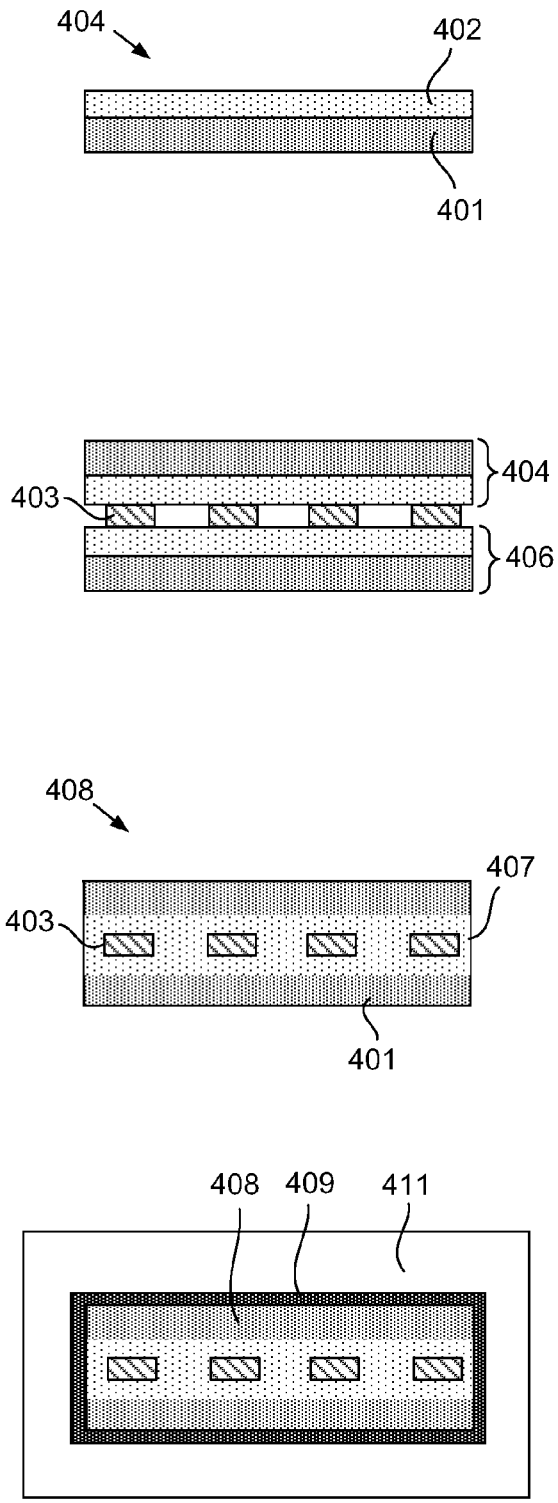
Fig. 4A
Fig. 4B

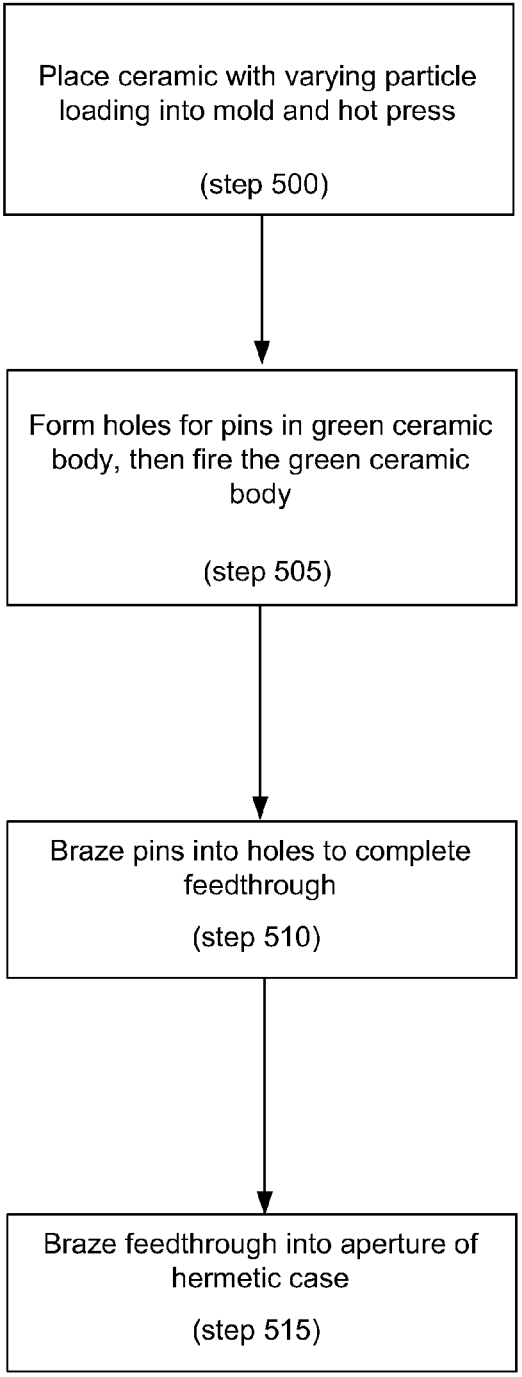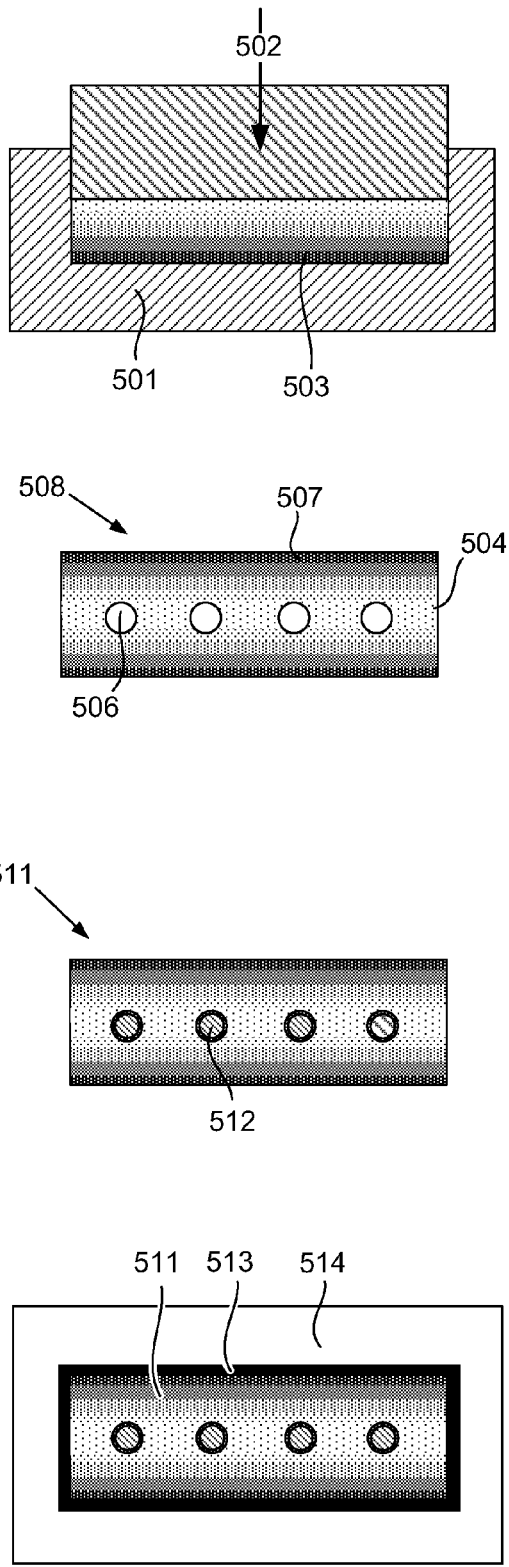
Fig. 5A
Fig. 5B

PARTICULATE TOUGHENED CERAMIC FEEDTHROUGH

RELATED DOCUMENTS

The present application claims the benefit under 35 U.S.C. §371 to International PCT application No.: PCT/US 2011/064876 filed Dec. 14, 2011 which claims the benefit under 35 U.S.C. §119(e) of U.S. Provisional Application No. 61/423,355, entitled "Particulate Toughened Ceramic Feedthrough" filed Dec. 15, 2010, which applications is incorporated herein by reference in their entirety.

BACKGROUND

Hermetically sealed cases can be used to isolate electronic devices from environmental contamination. To form electrical connections between the interior and the exterior of a hermetically sealed case, a hermetic feedthrough can be used. Ideally this hermetic feedthrough would maintain the integrity of the hermetic sealed case, while allowing electrical signals to pass through. Ceramic can be used to form the body of the feedthrough, with a number of electrically conductive pins passing through the ceramic. Ceramic has a number of benefits, including resistance to chemical corrosion, high strength, and fluid/vapor impermeability. However, the reliability of the ceramic body in hermetic feedthrough can become a limiting factor in some implant designs.

BRIEF DESCRIPTION OF THE DRAWINGS

The accompanying drawings illustrate various embodiments of the principles described herein and are a part of the specification. The illustrated embodiments are merely examples and do not limit the scope of the claims.

FIG. 4A is a flowchart of an illustrative method for creating particulate toughened ceramic feedthroughs, according to one example of principles described herein.

FIG. 4B shows illustrative cross-sectional diagrams that correspond to the illustrative method of FIG. 4A, according to one example of principles described herein.

FIG. 5A is a flowchart of an illustrative method for creating particulate toughened ceramic feedthroughs with brazed pins, according to one example of principles described herein.

FIG. 5B shows illustrative cross-sectional diagrams that correspond to the illustrative method of FIG. 5A, according to one example of principles described herein.

Throughout the drawings, identical reference numbers designate similar, but not necessarily identical, elements.

DETAILED DESCRIPTION

Human implant technologies often make use of implanted electronic devices. Hermetically sealed cases are used to protect electronic components in the implants from bodily fluids and various mechanical forces. As mentioned above, an electrical feedthrough maintains the integrity of the hermetically sealed case, while allowing electrical signals to pass through. The electrical feedthrough is often constructed as a separate element and then sealed into an aperture in a wall of an implant housing.

One of the determining factors for the impact resistance of the implant is the toughness of the feedthrough. For example, an implanted processor of a cochlear implant is typically located above and behind the external ear. Impacts to the head of the user can create significant loads on the implanted processor and the feedthroughs that pass electrical signals between the internal components of the implanted processor and other devices.

As used in the specification and appended claims, the term "ceramic" is used broadly and does not distinguish between glass, glass ceramic, ceramic composites and other types of ceramic materials. Ceramic can form the body of the feedthrough, with a number of electrically conductive pins passing through the ceramic. The ceramic has a number of benefits, including resistance to chemical corrosion, high strength, fluid and vapor impermeability, and other advantages. However, ceramic can exhibit low fracture toughness. This can lead to hermetic failures of the ceramic from crack propagation. Toughening the ceramic by including engineered microstructures can significantly reduce hermetic failure of the feedthrough.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Figure 1:
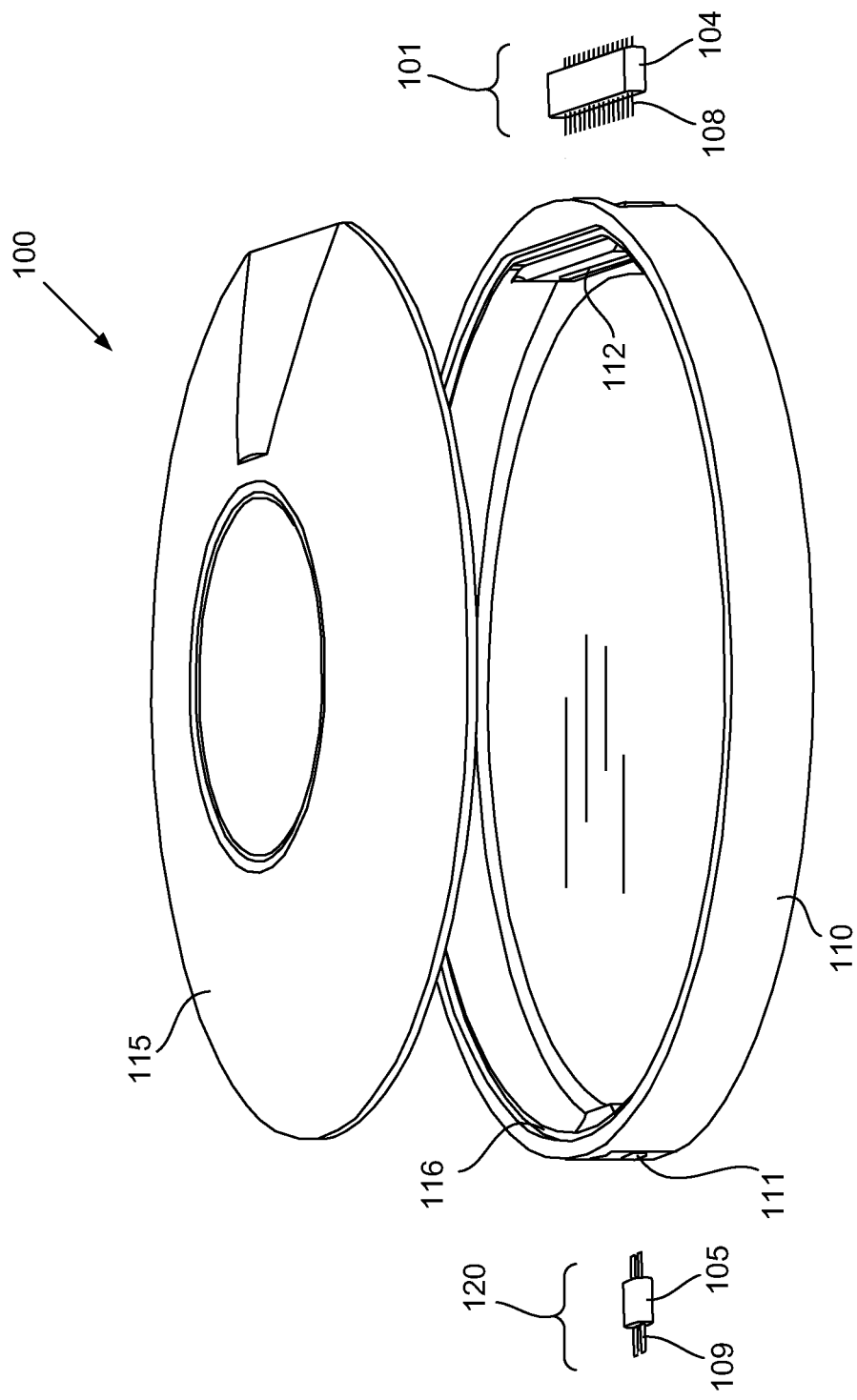
FIG. 1 is an exploded view of an illustrative hermetically sealed case, according to one example of principles described herein.

FIG. 1 is an exploded view of an illustrative hermetic enclosure (100) that houses cochlear implant electronics. In this particular example, the hermetic enclosure (100) includes a case (110) and a case top (115). The case (110) and the case top (115) may be formed from a variety of biocompatible materials. For example, the case (110) and case top (115) may be formed from metals, ceramics, crystalline structures, composites, or other suitable materials. The outer case (110) may be formed from a single piece of material or may include multiple elements. The multiple pieces may be connected through a variety of methods including, but not limited to, brazing, laser welding, or bonding.

According to one illustrative example, the case (110) and the case top (115) are formed from titanium. Titanium has a number of desirable characteristics, including high strength, resiliency, biocompatibility, low density, and low permeability. The case (110) shown in FIG. 1 is a closed-bottom cylinder that is machined, stamped, or otherwise formed from a single piece of titanium. In this example, the case (110) includes two apertures (111, 112) that are configured to receive hermetic electrical feedthroughs (101, 120). The case top (115) is also made from titanium and can be placed onto a ledge (116) machined into the upper rim of the case (110). The case top (115) can then be laser welded or brazed onto the case (110). Once the case top (115) and hermetic electrical feedthroughs (101, 120) are in place, the hermetic enclosure (100) prevents liquids or gasses from entering the interior of the enclosure (100). As discussed above, this prevents damage to electronics or other components housed in the interior of the hermetic enclosure (100).

The electrical feedthroughs (101, 120) may be formed from a variety of materials and have a number of different configurations. According to one illustrative example, the electrical feedthroughs (101, 120) include a set of conductors (108, 109) that are imbedded in ceramic bodies (104, 105). The conductors (108, 109) pass through and are sealed in the ceramic body. The sealing of the conductors to the ceramic body may take place in a variety of ways, including gold brazing or partial transient liquid phase (pTLP) bonding.

The ceramic body (104, 105) is then joined to the appropriate aperture (111, 112) in the case (110). A variety of techniques, including gold brazing, can be used to join the ceramic body to the case (110). In this illustrative example, the hermetic feedthroughs (101, 120) are on the perimeter of the case (110). Although the feedthroughs (101, 120) are illustrated as being located in the perimeter of the case (110), the feedthroughs could also be formed at other locations on the case (110) or the case top (115). Additionally, the number and size of hermetic feedthroughs (101,120) could be varied according to the design requirements. For example, a single feedthrough could be used to make all the electrical connections with the internal electronics.

Figure 2A:
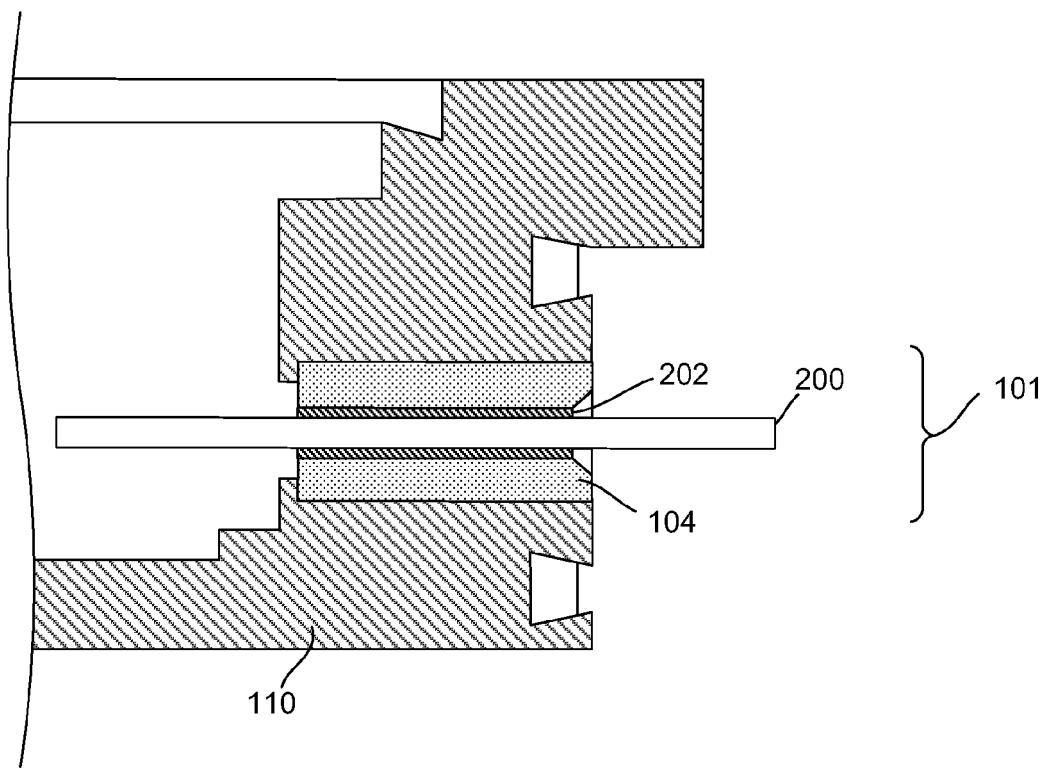
FIG. 2A is a cross-sectional view of an illustrative electrical feedthrough that includes conductive pins that are hermetically sealed into a ceramic body using a gold braze joint, according to one example of principles described herein.
Figure 2B:
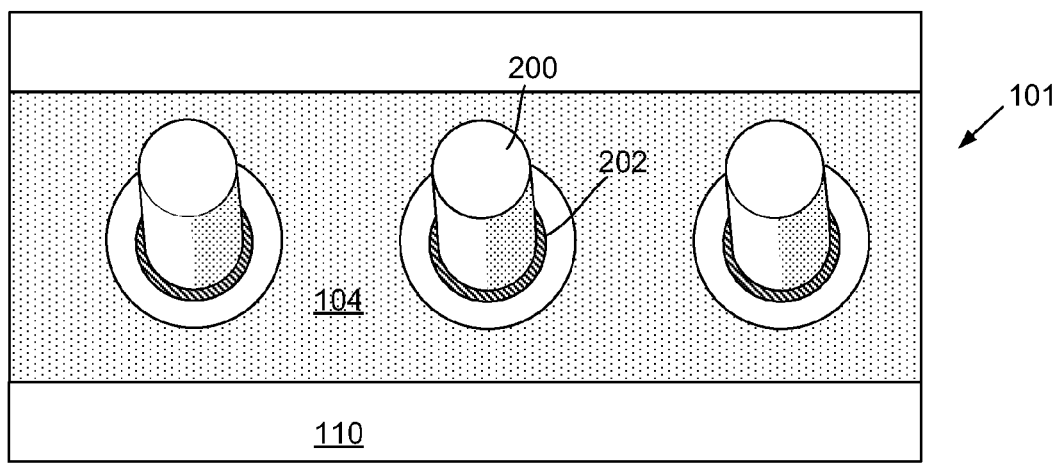
FIG. 2B is a perspective view of the illustrative electrical feedthrough shown in FIG. 2A, according to one example of principles described herein.

FIGS. 2A and 2B illustrate a feedthrough (101) that includes cylindrical pins (200) that are sealed into the ceramic body (104) using a gold braze joint (202). FIG. 2A is a cross-sectional view of a portion of the case (110) that includes the feedthrough (101). The left side of the pin (200) is connected to components that are internal to the case (110) and the right side of the pin (200) is connected to components that are external to the case (110). As used in the specification and appended claims, the term "pin" refers to an electrically conductive channel between the exterior and interior of a hermetic feedthrough. The pin (200) may have a variety of geometries and may be formed from a number of materials. For example, a pin may have a wide variety of shapes including circular, square, rectangular, elliptical, irregular, or other shapes. Further, in some examples such as co-axial feedthroughs, pins may be nested within other pins. In this example, the pins (200) are cylindrical and formed from platinum or a platinum alloy such as platinum iridium.

FIG. 2B is a perspective view of a portion of the hermetic case (110) that includes part of the hermetic feedthrough (101). As discussed above, the ceramic body (104) surrounds the pins (200) and is joined to the pins with a gold braze joint (202). The gold braze joint (202) may be formed in a variety of ways. For example, the gold braze joint (202) may be formed by placing the platinum pins through holes in a fully densified ceramic body (104). The platinum pins (200) and ceramic body (104) are heated and melted gold or a gold alloy is drawn by capillary action into the gap between the platinum pin (200) and the ceramic body (104).

In an alternative example, two or more green ceramic layers are used to form the ceramic body. These green ceramic layers could be formed in a variety of ways, including, but not limited to, tape casting, ceramic injection molding, or die pressing. The pins (200) are coated with a layer of gold around their circumference and laid on a bottom green ceramic layer. An upper green ceramic layer is laid over the pins (200) and the bottom layer. This sandwiches the gold coated pins between two layers of green ceramic. The green ceramic is then densified by the application of heat and pressure. This also joins the upper and lower layers and melts the gold to form a hermetic seal between the ceramic (104) and the pins (200).

A perimeter or surface of the ceramic body (102) can be joined to the hermetic case (110) in a number of ways, including brazing, active metal brazing, ceramic/metal joining, transient liquid phase bonding, or other suitable techniques.

Ceramic is typically considered a brittle material. Brittle materials exhibit very little plastic deformation prior to failure. Cracks tend to propagate long distances through brittle materials with little warning. Further, predicting where and when brittle materials will fail is difficult. As discussed above, the reliability of the ceramic body can become a limiting factor in some implant designs. For example, the ceramic body can be fractured through its thickness. This can destroy the hermetic seal and create an opening for the passage of fluids and/or gasses into the case. There are a number of mechanisms through which cracks can propagate in a ceramic. A first crack propagation mechanism results from the application of forces that exceed the local yield strength of the ceramic material. For example, these forces may be generated by mechanical impact or temperature changes that cause differential expansion of components in the device.

Crack propagation typically begins at a flaw or discontinuity in the ceramic. The flaw or discontinuity may be a scratch, indentation, inclusion, devitrified region, bubble, edge, corner, grain boundary, or other discontinuity in the ceramic. The flaw or discontinuity creates stress concentrations when the ceramic is subject to mechanical stress. These stress concentrations create situations where the ceramic body fails at stresses that are far below levels predicted by the ceramic's theoretical strength.

When the stresses concentrated by the flaw exceed the local yield strength of the ceramic material, the crack forms at the flaw and begins to propagate through the ceramic. The crack tip then concentrates the stress. Continued application of stresses that cause forces greater than the fracture strength of the material at the crack tip results in propagation of the crack. Large cracks in the ceramic can compromise the sealing, electrical, and mechanical properties of the feedthrough. The fracture toughness of a ceramic material is a measure of its resistance to facture when forces are applied.

Another failure mechanism in ceramic materials is stress corrosion cracking. Stress corrosion cracking often works in concert with crack propagation caused by the application of mechanical forces. Stress corrosion cracking occurs when a crack tip or other flaw is attacked by the environment. The crack tip is particularly sensitive to chemical corrosion because of the concentrated levels of stress in the material near the crack tip. This environmental attack weakens the material near the crack tip and results in the continued propagation of the crack. Stress corrosion cracking has been clearly demonstrated in wet and humid environments for silicate glasses and for aluminum oxide. This makes stress corrosion cracking particularly relevant for implanted feedthroughs.

A number of illustrative examples for toughening ceramic bodies used in feedthroughs are described below. These methods include metallic particle reinforcement and the creation of toughening microstructural elements. The principles described herein are discussed in the context of implantable feedthroughs. However, the principles described are broadly applicable to ceramics bodies in a variety of applications.

Intrinsic toughening mechanisms are typically active in ductile materials and are damage mechanisms that primarily occur ahead of the crack tip and increase the material's resistance to fracture, e.g., plasticity. Extrinsic toughening mechanisms are active in brittle materials and are principally present in the wake of a crack and reduce the driving force for crack extension at the tip of the crack, e.g., bridging, deflection, twist, microcracking, etc.

The fracture resistance and stress corrosion crack-growth resistance in ceramics can be improved by enhancing extrinsic toughening mechanisms or introducing new toughening mechanisms. As used in the specification and appended claims the term "mitigate" or "mitigating" crack propagation refers to inhibiting, deflecting, arresting, or otherwise reducing crack propagation through the ceramic. For example, ductile metal particles in the ceramic may bridge a crack and reduce the stress concentration at the tip of the crack. This can significantly reduce the crack propagation. These metallic reinforcements can be selected based on a variety of criteria, including their ability to bond to the ceramic matrix, their effectiveness at volume fractions well below the percolation threshold, biocompatibility, corrosion resistance, and their compatibility with ceramic fabrication techniques. The volume fraction of the metallic reinforcing phase is selected to provide the desired toughening without risk of shorting between conductive pins in the feedthrough. The risk of shorting varies according to a number of factors including: the dielectric properties of the matrix materials; the geometry of the metallic reinforcing phase; the voltage applied to the pins; spacing between adjacent pins; the current applied through the pin; and other factors. For example, where the feedthrough is used in an implantable defibrillator, voltages of approximately 1000 Volts and energies of 40 Joules can be applied. Particulate reinforcements in feedthroughs for this application may be spaced farther apart than particulate reinforcements in feedthroughs for lower energy applications such as a cochlear implant.

Figure 3:
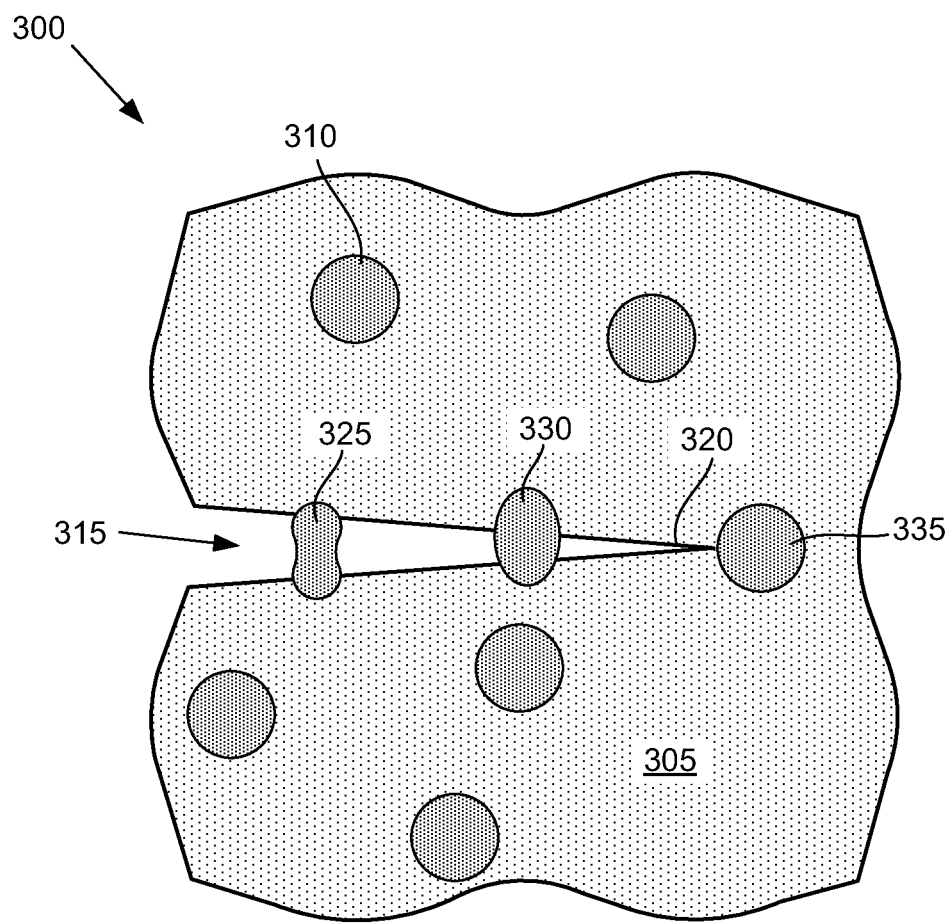
FIG. 3 is a cross-sectional view of an illustrative ceramic body with interspersed ductile particles, according to one example of principles described herein.

FIG. 3 shows a portion of a ceramic feedthrough body (300) that is made up of a ceramic matrix (305) with interspersed ductile particles (310). The ceramic matrix (305) could be formed from a variety of biocompatible materials including alumina, zirconium, alumina-based ceramics, and other suitable materials.

To maintain the biocompatibility of the ceramic feedthrough (300) after crack propagation begins, the interspersed ductile particles (310) can be formed from a biocompatible material such as platinum or a platinum alloy. A variety of other chemically stable and bio-inert materials that exhibit plastic deformation could also be used.

A crack (315) is shown propagating through the ceramic matrix (305). The ceramic matrix (305) fractures in a brittle fashion, but the ductile particles (310, 325, 330, 320) are plastically deformed by the crack. Metal particles in the plastic zone of the crack will be deformed and dissipate energy. In the wake of the crack, the particles will form a process zone and will continue to plastically deform and hold the crack faces closed until rupture of the particles. The amount of toughening that can be achieved by such methods is significant and a greater than two-fold increase in the toughness of the ceramic is possible.

In general, the particles can be selected to have a wide range of aspect ratios and geometries. For example, the metallic particles may have a variety of shapes and sizes. The particles illustrated in FIG. 3 have aspect ratios that are generally the same in all dimensions. These particles could be spherical, cubic, or other compact shapes. Some particles may have high aspect ratio in one dimension, such as rods, cones, and fibers. Other particles may have higher aspect ratios in two dimensions, such as plates or disks. In some examples, multiple types of particles could be incorporated into a single feedthrough.

Where the particles have higher aspect ratios in one or more dimensions, the particles could be advantageously oriented throughout the matrix. For example, high aspect ratio particles could be oriented using extrusion, casting, rolling, pressing, or injection molding. The particle shape may also be influenced by a number of factors, including the plastic deformation that occurs during pressing, firing, melting and resolidification, etc The yield strength of the metallic reinforcements can also be selected to provide maximum toughness. A low yield stress will result in a large plastic zone and a high yield strength will provide more effective bridges in the process zone. In some examples, two or more types of metallic particles with different yield strengths could be incorporated into a feedthrough.

In this example, the crack has propagated past two of the ductile particles (325, 330). These ductile particles (325, 330) form bridges across the crack. These bridges hold the two sides of the crack together and resist further spreading of the crack. This can significantly reduce forces at the crack tip. The crack tip (320) has encountered a third ductile particle (335). The third ductile particle (335) tends to diffuse the stress that is concentrated at crack tip (320) and allows the ceramic material to resist higher loading before the crack tip (320) continues to propagate.

The dispersed ductile particles (310, 325, 330, 335) may also help mitigate the effects of stress corrosion cracking. As discussed above, the ceramic matrix (305) may be attacked by corrosive solutions in the implanted environment. Portions of the ceramic matrix that are under higher levels of stress are more vulnerable to stress corrosion. Because the geometry at the crack tip causes stress concentrations, the crack tip is particularly vulnerable to stress corrosion. As the ceramic material at the crack tip is corroded, it becomes weaker and allows the crack to propagate at lower and lower stress levels. However, the inclusion of ductile particles that are corrosion resistant can reduce the stress concentrations at the crack tip while being unaffected by the corrosive environment. For example, platinum particles in an alumina matrix are very corrosion resistant and have significant ductility. Consequently, the inclusion of platinum particles into an alumina matrix can increase the fracture toughness of the ceramic feedthrough body by bridging the crack to reduce strain energy in the crack, reducing stress concentrations at the crack tip, and resisting corrosion.

There are a number of methods for creating and distributing the particles, layers, or other microstructures within the ceramic. These methods may include die pressing ceramic powder with successive particle loading; slurry deposition on a green ceramic body; and various coatings on ceramic bodies, e.g., CVD, sputtering, evaporation. The thickness of layers and coatings could be varied. In some examples, the fracture toughness mechanisms can be enhanced by using processes that generate appropriate residual compressive stresses.

In the case of alumina, various powder techniques can be used form the green bodies used to make the feedthrough. For example, tape casting, die pressing, powder injection molding, etc. can be used to make the green body. The metallic particles can be selectively mixed in the powder and formed into green bodies made using these techniques.

The example of alumina matrix with platinum particles given above is only one illustrative example. A variety of matrix and particle combinations could be used. The size of the particles and volume fraction of the particles can be varied throughout the structure. In some examples, more than one type of particle can be used. In designing and creating the particles within the ceramic, care should be taken to avoid particle sizes or concentrations that create undesired conductive paths between pins that pass through the ceramic body or between pins and the surrounding case.

Depending on the selected processing route it may be advantageous to choose a metal with a melting temperature above or below the firing temperature of the ceramic. Examples of metallic materials that can be used as part of the particulate phase include, Pt, Nb, Ti, CoCr, Ni, Au, and other suitable metals, alloys, or metal combinations. Where alumina is used as the ceramic matrix, gold, some gold alloys, some niobium/platinum alloys and other alloys could have lower melting points than the alumina firing temperature. Platinum, titanium and nickel are examples of metals that have melting points that are higher than typical alumina firing temperatures. In some examples, techniques such as power metallurgy, partially transient liquid phase bonding and fully transient liquid phase bonding can be used to create strong bonds between the metallic phase and the ceramic. In some examples, the particles may also employ or activate self healing chemistry to mitigate crack propagation.

One example of partially transient liquid phase bonding is the use of platinum particles coated with niobium embedded in the ceramic matrix. The platinum has a high melting point and the niobium has a lower melting point. During processing, the niobium melts and forms a liquid phase of a niobium/platinum alloy on the surface of the platinum. This liquid phase wets the ceramic and creates a strong bond between the ceramic and the platinum particle. The niobium then rapidly diffuses from the surface of the platinum into the platinum particle. This changes the composition of the liquid phase and raises its melting point. Consequently, the liquid phase solidifies after a short period of time. Niobium is just one example of an additive that can be used at grain boundaries between the ductile particles and the ceramic matrix. A variety of other additives could be used.

The introduction of metallic particles into feedthrough bodies is against conventional wisdom because the metallic particles can form electrical shorts between the pins or between the pins and the case. However, as shown below, the particulates may be selectively distributed throughout the ceramic feedthrough body using a number of techniques that can eliminate shorting between the pins or between the pins and the case.

FIG. 4A is a flowchart of an illustrative method for creating a particulate toughened ceramic feedthrough. FIG. 4B shows illustrative cross sectional diagrams that correspond to the illustrative method of FIG. 4A. In this example, a first ceramic body (404) is created by joining a first layer (402) with a low concentration of ductile particles with a second layer (401) that has a higher density of particles (step 400). For example, a quantity of ceramic powder (401) with a known concentration or distribution of metallic particles can be introduced into a mold and hot pressed. A second quantity of ceramic powder (402) with metallic particles can be added to the mold and pressed over the first ceramic powder. This creates a ceramic body (404) with a high quantity of metallic particles in a first area and a lower quantity of metallic particles in a different area. A second body (406) is formed in using the same technique.

Pins (403) are sandwiched between two of these bodies (404, 406), with the pins contacting the portions with the lower quantity of metallic particles (step 405). The assembly is then fired to join the layers and densify the ceramic to create the feedthrough (408) (step 410). Because the pins (403) are in direct contact with only a central portion of the ceramic (407) that has lower quantities of metallic particles, the chances of the pins (403) shorting is minimized. Before the hermetic feedthrough (408) is joined to the case (411), it can be tested to determine if the pins are appropriately insulated from each other. The hermetic feedthrough can be joined to the case in a variety of ways, including using a braze joint (409) (step 415). After brazing of the feedthrough (408) into the hermetic case (411), the pins (403) can again be tested to determine if any of the pins is shorted to the case or each other.

FIG. 5A is a flowchart of an alternative method for creating particulate toughened ceramic feedthroughs with brazed pins. FIG. 5B shows illustrative cross sectional diagrams that correspond to the illustrative method of FIG. 5A. In this example, ceramic (503) with varying particle loading is placed in a mold (501) and hot pressed as shown by the arrow (502) (step 500). This process is continued until a green ceramic body (508) is formed with higher particulate densities in the outer layers (507) and lower particulate densities in the central layers (504). Holes (506) are formed through the green ceramic body (508) and the green ceramic body (508) is fired (step 505). Pins (512) are brazed into the holes (step 510) to form feedthrough (511). The feedthrough (511) is then brazed into an aperture of the hermetic case (step 515). The braze joint (513) surrounds the feedthrough (511) around its perimeter. As discussed above, the feedthrough (511) could be placed in compression during the braze process. This compressive stress can potentially reduce crack driving forces.

Other examples of methods that could selectively distribute the metallic particles through the ceramic matrix include ceramic injection molding, tape casting or other techniques that allow the pins to be surrounded by ceramic with lower concentrations of particulates and the other areas to have higher densities of particles. For example, a high density green ceramic tape and a low density green ceramic tape could be formed. The pins could be sandwiched between two segments of green ceramic tape that contain low densities of metal particles. This assembly could then be sandwiched between two green ceramic tapes that have higher densities of metal particles. In some examples, a green body could be pressed into shape and then a dry slurry could be deposited over the green body or vice versa. These techniques allow for varying densities of particulates to be created within a ceramic body.

In some examples, particulates of varying properties, size, and geometry may be used in a single ceramic feedthrough. For example, nonconductive ductile particles may be used in proximity to the pins and ductile metallic particles may be used in other locations. In an other embodiment, smaller particles relatively uniform aspect ratios could be used in proximity to the pins to reduce the chances of creating an undesired conductive path. Higher aspect ratio particles such as rods or plates may be used farther away from the pins.

Figure 6:
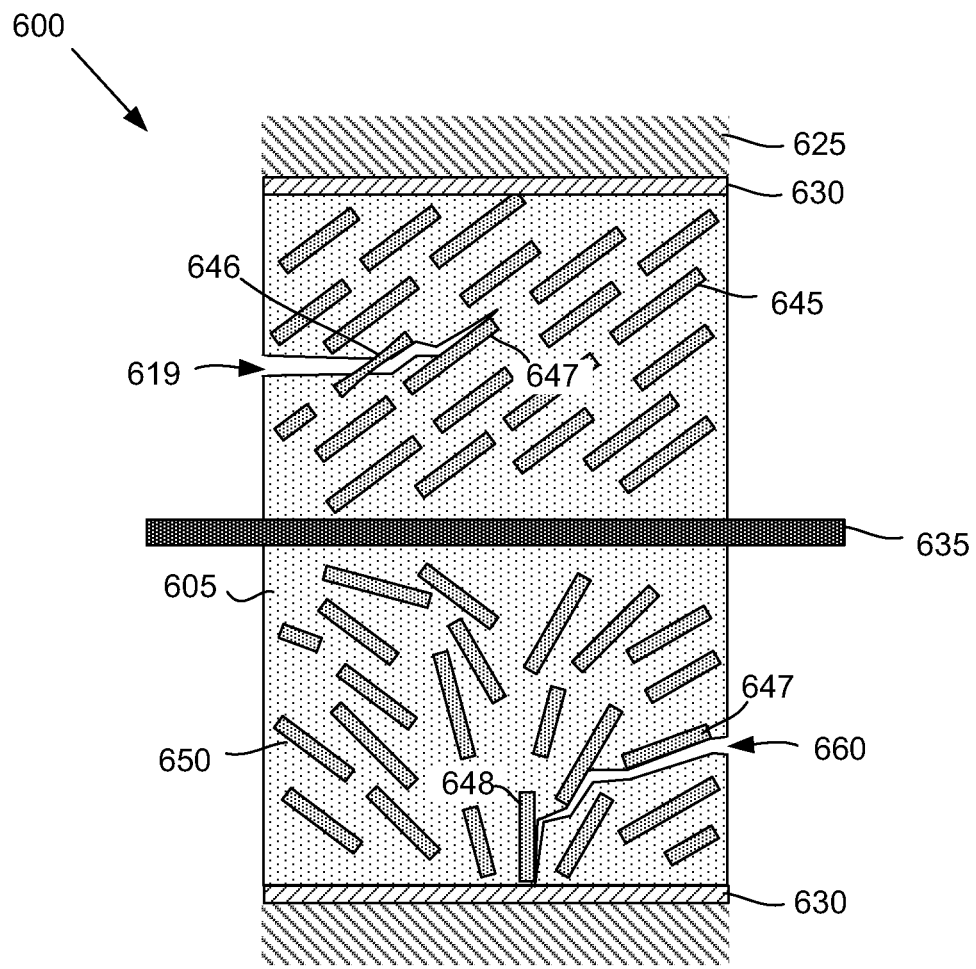
FIG. 6 is a cross-sectional diagram of illustrative toughening particulates in ceramic bodies, according to one example of principles described herein.

FIG. 6 is a diagram of illustrative toughening particulates (645) in a ceramic feedthrough (600). In FIG. 6, a number of high aspect ratio particles (645) are distributed throughout the ceramic matrix (605). In this illustrative example, the high aspect ratio particles (645, 650) are ductile and create diversion planes that preferentially direct crack propagation. The technique of using crack diversion planes in ceramic feedthrough bodies is described in U.S. App. No. 61/423,337, filed on Dec. 15, 2010, entitled "Crack Diversion Planes in Ceramic Feedthroughs," to Kurt Koester, which is incorporated herein by reference in its entirety.

In the upper half of the ceramic matrix (605), the high aspect ratio particles (645) have a relatively uniform orientation throughout the ceramic matrix (605). As a crack (619) propagates through the matrix (605), it encounters the high aspect ratio particles (645). A first high aspect ratio particle (646) does not deflect the crack (619) but bridges the gap and reduces the driving force. A second particle (647) deflects the crack path. Both of these actions increase the toughness of the feedthrough (623).

The lower half of the ceramic matrix (605) has high aspect ratio particles (650) that have more variation in their orientation within the matrix. In this illustrative example, the high aspect ratio particles (650) near the left and right sides of the feedthrough (600) have more perpendicular orientations with respect to the faces of the feedthrough. The orientation of the high aspect ratio particles gradually transitions toward the center of the feedthrough to orientations that are more parallel with the left and right faces. Particles with more perpendicular orientations may have an increased chance of diverting the crack as it begins to propagate from the surface. The particles with parallel orientations may be more effective in directing the cracks approaching from either direction toward the braze material. For example, first particle (647) has diverted crack (660) as it began to propagate and a second particle (648) directed the crack into the braze material (630). When the crack encounters the braze material (630), the growth of the crack may be arrested by the ductile braze material (630).

The high aspect ratio particles may be formed within the matrix in a number of ways, including powder injection molding, tape extrusion, or a variety of coating methods. The high aspect ratio particles may be oriented using a number of methods, including extrusion, rolling, stamping, or other method. The high aspect ratio particles may be oriented in variety of configurations, including those shown in FIG. 6. Other examples may include helical, chevron, or other particle orientations. In some examples, the high aspect ratio particles may be used without subsequent orientation and may have a more random orientation than shown in FIG. 4E. The high aspect ratio particles may also serve as crack dividers, as described in "Crack Diversion Planes in Ceramic Feedthroughs," to Kurt Koester, which was incorporated by reference above.

In sum, the toughness of ceramic materials used for feedthroughs can be improved by incorporating ductile particulates in the ceramic. These ductile particulates may include metallic particles that are selectively distributed through the ceramic to prevent shorting between pins or between the pins and the hermetic case.

The preceding description has been presented only to illustrate and describe examples and examples of the principles described. This description is not intended to be exhaustive or to limit these principles to any precise form disclosed. Many modifications and variations are possible in light of the above teaching.

What is claimed is:

1. A feedthrough comprising:
   a hermetic case; and
   a ceramic body mechanically joined about a perimeter to the hermetic case, the ceramic body comprising:
      a ceramic matrix;
      a ductile phase distributed through at least a portion of the ceramic matrix, the ductile phase being configured to increase the resistance of the ceramic matrix to crack propagation, the ductile phase comprising electrically isolated particles; and
      a plurality of electrical conductors passing through the ceramic body.

2. The feedthrough of claim 1, wherein the ductile phase comprises metallic particles.

3. The feedthrough of claim 2, wherein the metallic particles are platinum or a platinum alloy.

4. The feedthrough of claim 2, wherein the metallic particles are configured to bridge gaps created by a crack through the ceramic body to reduce the driving force of the crack.

5. The feedthrough of claim 2, wherein the metallic particles comprises particles with a higher aspect ratio in two dimensions than in a third dimension.

6. The feedthrough of claim 5, wherein the metallic particles have a substantially uniform orientation in the ceramic body.

7. The feedthrough of claim 5, wherein the metallic particles are configured to plastically deform while bridging gaps created by a crack and are oriented to preferentially inhibit crack propagation trajectories through the ceramic body.

8. The feedthrough of claim 1, wherein a lower concentration of the ductile phase is disposed in portions of the ceramic matrix adjacent to the plurality of electrical conductors and a higher concentration of the ductile phase is disposed in portions of the ceramic matrix away from the plurality of electrical conductors.

9. The feedthrough of claim 1, wherein the feedthrough is a component of an implantable device.

10. The feedthrough of claim 9, wherein the hermetic case is a processor case.

11. The feedthrough of claim 1, wherein the ductile phase comprises platinum particles with an outer coating of niobium.

12. A method for forming the feedthrough of claim 1, the method comprising:
   forming the ceramic body with varying particle loading, the ceramic body having a first portion that has a low density of ductile particles and a second portion that has a higher density of ductile particles, wherein the ductile particles are electrically isolated;
   disposing conductive pins in the first portion of the ceramic body to form the plurality of electrical conductors passing through the ceramic body of the feedthrough; and
   joining the ceramic body to a hermetic case.

13. The method of claim 12, further comprising:
   forming holes in the ceramic body;
   firing the ceramic body; and
   brazing conductive pins into the holes.

14. The method of claim 12, wherein disposing conductive pins in the first portion of the ceramic body comprises sandwiching the pins between a first ceramic body and a second ceramic body with the pins being in contact with the portions of the first ceramic body and second ceramic body that have a low density of ductile particles.

15. The method of claim 12, wherein disposing the conductive pins in the first portion of the ceramic body comprises using partially transient liquid-phase bonding.

16. The method of claim 12, wherein the particles comprise platinum with an outer coating of niobium.

17. The method of claim 12, further comprising orienting high aspect ratio particles prior to firing the ceramic.

18. A feedthrough comprising:
   a hermetic case;
   a ceramic body mechanically joined about a perimeter to the hermetic case, the ceramic body comprising:
      a ceramic matrix;
      a ductile phase comprising individual particles distributed throughout and surrounded by at least a portion of the ceramic matrix, the ductile phase resisting crack propagation in the ceramic matrix, the ductile phase comprising discrete particles distributed throughout a thickness of the ceramic body; and a plurality of electrical conductors passing through the ceramic body.

19. The feedthrough of claim 18, wherein the ductile phase comprises platinum particles with an outer coating of niobium.

20. The feedthrough of claim 18, wherein the ductile phase comprises particles with a higher aspect ratio in two dimensions than in a third dimension.

* * * * *